US005292992A

United States Patent [19]

Belmont et al.

[11] Patent Number: 5,292,992

[45] Date of Patent: Mar. 8, 1994

[54] PROCESS FOR REMOVING CONJUGATED DIENES FROM ALPHA-OLEFINS

[75] Inventors: Stephen E. Belmont; Patrick G. Simms; Keith G. Anderson, all of Baton Rouge, La.

[73] Assignee: Ethyl Corporation, Richmond, Va.

[21] Appl. No.: 40,387

[22] Filed: Mar. 30, 1993

Related U.S. Application Data

[63] Continuation of Ser. No. 874,922, Apr. 28, 1992, abandoned.

[51] Int. Cl.$^5$ .................................................. C07C 7/12
[52] U.S. Cl. ..................................... 585/820; 585/832; 585/833; 585/852; 585/853
[58] Field of Search ............... 585/820, 832, 833, 852, 585/853

[56] References Cited

U.S. PATENT DOCUMENTS

| | | | |
|---|---|---|---|
| 3,758,608 | 9/1973 | Rigdon et al. | 585/822 |
| 4,689,437 | 8/1987 | Murray | 585/526 |
| 5,053,569 | 10/1991 | Marquis et al. | 585/255 |

OTHER PUBLICATIONS

CA85(4):22579c in German Offen. DE 2,535,818 Apr. 1, 1976 Butadiene is separated from other C$_4$ olefins by selective adsorption on zeolites (page unavailable).
CA78(17):110837w in German Offen. DE 2,236,996 Feb. 15, 9173 Olefins are removed from aromatic hydrocarbons by contact with Fitrol 24 clay at 110°–115° C (page unavailable).
Engelhard Exceptional Technologies–EC–5958–Grade F24 Absorbent Products–Product Bulletin (page unavailabe) (year unavailable).
Engelhard Exceptional Technologies–EC–5959–Grade F25 Absorbent Products–Product Bulletin (page unavailable) (year unavailable).
Engelhard Exceptional Technologies–Grade F34 Absorbent Products–Product Bulletin (page unavailable) (year unavailable).
Engelhard Exceptional Technologies–Grade F54 Adsorbent Products–Product Bulletin (page unavailable) (year unavailable).
Engelhard Exceptional Technologies–EC–5982–Grade F124 Absorbent Prodcts–Product Bulletin (page unavailable) (year unavailable).
Catalysts of Sud–Chemie AG–Product Bulletin (page & year unavailable).

*Primary Examiner*—Anthony McFarlane
*Assistant Examiner*—Nhat D. Phan
*Attorney, Agent, or Firm*—David M. Bunnell

[57] ABSTRACT

Conjugated diene impurities are removed from linear alpha-olefin products by contacting the linear alpha-olefin product with an acid treated montmorillonite clay which is effective to reduce the conjugated diene content of the linear alpha-olefin product, preferably to less than about 100 ppm, without substantial isomerization of the linear alpha-olefins to internal olefins.

10 Claims, No Drawings

PROCESS FOR REMOVING CONJUGATED DIENES FROM ALPHA-OLEFINS

This application is a continuation of application Ser. No. 07/874,922, filed Apr. 28, 1992, now abandoned.

BACKGROUND OF THE INVENTION

This invention relates generally to a quality improvement process for alpha-olefins and more specifically to a process for the removal of dienes from alpha-olefins, without substantial isomerization of the alpha-olefins to internal olefins, achieved by contacting the alpha-olefins with acid treated montmorillonite clays.

The preparation of linear, $C_4$ to $C_{30}$ alpha-olefin mixtures by ethylene chain growth using triethylaluminum followed by ethylene displacement is a well known process. The olefin type produced is mainly alpha-olefins, i.e., $R-CH=CH_2$, where R is an aliphatic hydrocarbon group but the product also contains small amounts of internal olefins, $R-CH=CHR$, where R is an aliphatic hydrocarbon group, vinylidene olefins $R_2C=CH_2$ where each R is an aliphatic hydrocarbon group and dienes which may be straight or branched chain conjugated dienes. The products can be separated into single or mixed carbon number olefins by distillation for selected end uses. Lower carbon number olefins such as hexene-1 and octene-1 are useful, for example, as comonomers in olefin polymerizations and the presence of impurities such as vinylidene olefins and conjugated dienes may interfere in such uses. It is therefore desirable to remove or reduce the amounts of these impurities. At the same time, the removal process should not substantially affect the alpha-olefin such as by converting it to other olefin species. We are aware that an acid clay treatment bed of some type has been used by others to remove cyclopentadiene, formed in connection with a catalytic polymerization process, from a recycle diluent stream.

SUMMARY OF THE INVENTION

In accordance with this invention, there is provided a process for improving the quality of a conjugated diene containing linear alpha olefin product, said process comprising contacting the linear alpha-olefin product with an acid treated montmorillonite clay which is effective to reduce the conjugated diene content of the linear alpha-olefin product without substantial isomerization of the linear alpha-olefin product to internal olefins.

DETAILED DESCRIPTION

The process of the invention is especially useful in the purification of alpha-olefin or mixed alpha-olefin products having from about five to thirty carbon atoms, and especially hexene-1 and octene-1. Conjugated diene containing alpha-olefin products from any source can be purified by the process of this invention. Alpha-olefins which are derived from ethylene chain growth processes usually contain from about 100 to 10,000 ppm, and more particularly from about 100 to 1000 ppm based on the total weight of product, of straight and/or branched chain conjugated dienes such as 1,3-octadiene, 3methyl-1,3-pentadiene, and/or 4-ethyl-I,3-hexadiene which dienes can interfere with end uses of the alpha-olefins. The alpha-olefins usually also contain minor amounts of vinylidene olefins and internal olefins. The process of the invention also removes the vinylidene olefins by converting them to tri-substituted olefins which are normally inert in polymerization reactions. The internal olefins in the products are less reactive than alpha-olefins and, although they usually do not interfere with alpha-olefin reactions, their presence deducts from the amount of material available to react. Accordingly, it is undesirable to isomerize any substantial amount of the alpha-olefins to internal olefins in the process of removing the conjugated dienes.

We have found that certain acid treated montmorillonite clays are active to reduce the conjugated diene content of linear alpha-olefin products to below about 100 ppm and, especially, to below 50 ppm, without substantial (less than about 5 wt percent, preferably less than 0.5 wt. percent and more preferably less than 0.05 wt. percent) isomerization of the alpha-olefins to internal olefins, provided that the clays contain a sufficient amount of water to minimize such isomerization. Too much water on the other hand, can deactivate the clay with respect to the removal of certain conjugated dienes, and especially straight chain conjugated dienes. Amounts of water, as determined by weight difference after heating the clay at 800° C. for 2 hours, of at least about 2 wt. percent are sufficient to avoid substantial isomerization. Amounts of water above about 20 wt. percent are unnecessary and, in order to provide reasonable activity in removing branched chain conjugated dienes, it is preferable to keep the water content at from about 5 to 15 wt. percent, depending upon the particular montmorillonite clay which is used. The water content of the alpha-olefin feed will also change the reactivity and should be controlled.

Montmorillonite clays are smectite clays which contain magnesium as a significant substitute for aluminum in the octahedral layer. A typical formula before activation is $[Al_{1.67}Mg_{0.33}(Na_{0.33})]$ $Si_4O_{10}(OH)_2$. The clays are activated by acid treatment, such as with mineral acids, to replace the alkali metal ions with hydrogen ions. The acid treated clays are commercially available and contain water. Only certain acid treated montmorillonite clays are useful in the process of the invention but, based on the teachings and illustrative examples contained herein, effective montmorillonite clays other than those specifically named herein can be identified. Illustrative examples of acid treated montmorillonite clays which have been found to be effective in the process of the invention include:

Englehard F-24 granular form, initial water content 19 wt. percent on a total weight basis, best activity at 11.6 wt. percent. (wt. loss at 800° C.), residual acidity 16 mg KOH/gm (at phenolphthalein endpoint), surface area (B.F.T. method) 350 m²/gm, effective particle size (calc) 0.48 mm; Englehard F-25 granular, free moisture, as wt. loss at 105° C., 12 wt. percent, residual acidity 16 mg KOH/gm, surface area 350 m²/gm, effective particle size 1.05 mm; Englehard G-62 granular, initial water content 12 wt. percent, best activity at 6.8 wt. percent (wt. loss at 800° C.); Englehard F-34 granular, free moisture, as wt. loss at 105° C., 14 wt. percent, residual acidity 20 mg KOH/gm, surface area 325 m²/gm, particle size >85 wt. percent passing 20 mesh Tyler sieve <5 wt. percent passing 60 mesh; Süd-Chemie AG K-10 powder, initial water content 11 wt. percent, best activity at 7.4 wt. percent (wt. loss at 800° C.), surface area (220-270 m²/g, residual acidity 330 micro equiv. free HCl; and Süd-Chemie AG KSF powder, initial water content 18 wt. percent, best activity at 14 wt. percent (wt. loss at 800° C.), surface area 10-30 m²/g, residual acidity 150 milliequiv. free $H_2SO_4$.

The partial drying of the clays to achieve maximum activity, and especially where branched chain conjugated dienes are to be removed, is preferably done at ambient temperatures, e.g. about 25° C., under vacuum, e.g. 0.1 to 2 mm Hg for about 2 hours. Drying under elevated temperatures of 100° to 800° C., and especially in combination with vacuum, may reduce the water content to the extent that excessive isomerization of alpha-olefins to internal olefins occurs. In fact, when the treatment process is done at elevated temperatures, e.g. 40° to 65° C., good removal rates of conjugated dienes can be achieved without pre-drying the clay. It may be necessary to either regenerate or replace the clay if the water content is reduced to the extent that excess isomerization of alpha-olefins to internal olefins is observed. The amount of clay used is not particularly critical and is selected to provide the desired degree of diene removal in a reasonable time.

The treatment of the alpha-olefin product can be done by mixing the alpha-olefin product in contact with the montmorillonite clay or by passing the alpha-olefin product through a packed bed of clay. Treatment temperatures usually range from about 15° C. to 70° C. with room temperature (about 25° C.) to about 65° C. being preferred. Temperatures of 70° C. tend to increase the isomerization of alpha-olefin to internal olefins. Contact times are selected to obtain the desired reduction in conjugated diene content and usually range from about 0.25 to 65 hr[-1] WHSV (weight hour space velocity).

The conjugated diene removal mechanism is not exactly known but it is believed that the clay catalyzes the reaction of conjugated diene with alpha-olefin to form diene dimers which are non-conjugated. Accordingly, the conjugated dienes are converted from active to relatively inert impurities. The dimers are present in small amounts so that they can remain in the product. They can be readily removed, if desired, by distillation of the product.

The invention is further illustrated by, but is not intended to be limited to, the following examples in which the term "diene" refers to conjugated dienes.

EXAMPLES 1-5

In Examples 1-5 octene-1 was treated of room temperature (25° C.) by mixing 10 cm³ of octene-1 with 1 gram of montmorillonite clay for 20 hours and the conjugated diene contents were determined by gas chromatographic analysis at 1 and 20 hours. The specific clays used and the results are given in Table 1. The total water content of the clays as determined by wt. loss after heating them at 800° C. for 2 hours was KSF, 18 wt. percent; K-10 powder 11 wt. percent; F-24 granular 19 wt. percent; and G-62 granular 12 wt. percent. The water content of F-25 was not determined but is believed to be similar to F-24.

TABLE 1

| | Octene-1 & Montmorillonite at Temp = 25° C. (10 cm³ Octene-1 and 1 g of Montmorillonite) | | | | |
|---|---|---|---|---|---|
| | | 1 hr | | 20 hrs | |
| Example | Clay | ppm diene | % 2-octene | ppm diene | % 2-octene |
| Control | None | 480 | 0.62 | 480 | 0.62 |
| 1 | Mont[1] KSF | 447 | NC[2] | 104 | NC |
| 2 | Mont K-10 | 251 | NC | 38 | NC |
| 3 | Mont F-24 | 282 | NC | 99 | NC |
| 4 | Mont F-25 | 248 | NC | 95 | NC |

TABLE 1-continued

| | Octene-1 & Montmorillonite at Temp = 25° C. (10 cm³ Octene-1 and 1 g of Montmorillonite) | | | | |
|---|---|---|---|---|---|
| | | 1 hr | | 20 hrs | |
| Example | Clay | ppm diene | % 2-octene | ppm diene | % 2-octene |
| 5 | Mont G-2 | 292 | NC | 73 | NC[3] |

[1]Mont = Montmorillonite
[2]NC = no change
[3]initial % 2-octene = 0.44

EXAMPLES 6-10

In Examples 6-10 hexene-1 was treated at room temperature (25° C. by mixing 10 cm³ of hexene-1 with 1 gram of montmorillonite clay for 20 hours and the conjugated diene contents were determined at 1 and 20 hours. The clays used were the same as for Example 1-5 and the results are given in Table 2. The results show that the reduction in conjugated diene content was slow, probably due to the fact that straight chain conjugated dienes were present in the hexene-1 feed.

TABLE 2

| | Hexene-1 & Montmorillonite at Temp = 25° C. (10 cm³ Hexene-1 and 1 g of Montmorillonite) | | | | |
|---|---|---|---|---|---|
| | | 1 hr | | 20 hrs | |
| Example | Clay | ppm diene | % 2-hexene | ppm diene | % 2-hexene |
| Control | None | 200 | 0.70 | 200 | 0.70 |
| 6 | Mont[1] K-10 | 195 | NC[2] | 158 | NC |
| 7 | Mont KSF | 195 | NC | 81 | NC |
| 8 | Mont F-24 | 195 | NC | 165 | NC |
| 9 | Mont F-25 | 194 | NC | 163 | NC |
| 10 | Mont G-62 | 200 | NC | 177 | NC |

[1]Mont = Montmorillonite
[2]NC = no change

EXAMPLES 11-20

In Examples 11-20 and the two comparative examples, octene-1 was treated as in Example 1 except that the clays were subjected to a heat and/or vacuum treatment (about 1 mm Hg) for 2 hours prior to use to reduce the water content. The results are given in Table 3 and show that heating the clays prior to use can cause excessive isomerization. Vacuum treatment at room temperature is preferred because it gives improved conjugated diene removal activity without causing substantial isomerization. With respect to the amount of water in the clays, samples of the clays which were similarly treated with vacuum at room temperature gave the following water content results, as determined by wt. difference after heating them at 800° C. for 2 hrs., K-10 7.4 wt. percent water; KSF 14 wt. percent water; F-22 11.6 wt. percent water and G-62 6.8 wt. percent water.

TABLE 3

| | Octene-1 & Activated Montmorillonite at Temp = 25° C. (10 cm³ Octene-1 and 1 g of Montmorillonite) | | | | |
|---|---|---|---|---|---|
| | | 1 hr | | 20 hrs | |
| Example | Clay/Activation | ppm diene | % 2-octene | ppm diene | % 2-octene |
| Control | None | 480 | 0.70 | 480 | 0.70 |
| 11 | Mont[1] K-10/800° C. | 71 | 0.79 | 36 | 0.79 |
| 12 | Mont F-24/800° C. | 35 | 0.74 | 18 | 4.4 |
| 13 | Mont K-10/200° C./vac | 26 | 1.06 | 11 | 3.11 |
| 14 | Mont KSF/200° C./vac | 384 | 0.91 | 54 | 1.26 |

TABLE 3-continued

Octene-1 & Activated Montmorillonite at Temp = 25° C.
(10 cm³ Octene-1 and 1 g of Montmorillonite)

| | | 1 hr | | 20 hrs | |
|---|---|---|---|---|---|
| Example | Clay/Activation | ppm diene | % 2-octene | ppm diene | % 2-octene |
| 15 | Mont K-10/100° C./vac | 9 | 1.05 | 8 | 3.35 |
| 16 | Mont KSF/100° C./vac | 327 | 0.72 | 59 | 0.82 |
| 17 | Mont K-10/vac | 61 | NC² | 12 | NC |
| 18 | Mont KSF/vac | 179 | NC | 35 | 0.73 |
| 19 | Mont F-24/vac | 20 | NC | 20 | 0.79 |
| 20 | Mont G-62/vac | 38 | NC | 37 | 0.47³ |
| Comparison | Mont F-24/200° C./vac | 17 | 7.2 | 0 | 28.0 |
| Comparison | Mont F-24/100° C./vac | 8 | 4.4 | 0 | 25.2 |

¹Mont = Montmorillonite
²NC = no change
³initial % 2-octene = 0.44

EXAMPLES 21-30

In Examples 21-30 hexene-1 was treated in accordance with the procedure of Examples 11-20. The results are similar as shown by the results given in Table 4. The results show the activity advantage achieved by vacuum drying of the clay compared to Examples 6-10 and that drying with heat and vacuum combined can cause excessive isomerization.

TABLE 4

Hexene-1 & Activated Montmorillonite at Temp = 25° C.
(10 cm³ Hexene-1 and 1 g of Montmorillonite)

| | | 1 hr | | 20 hrs | |
|---|---|---|---|---|---|
| Example | Clay/Activation | ppm diene | % 2-hexene | ppm diene | % 2-hexene |
| Control | None | 200 | 0.70 | 200 | 0.70 |
| 21 | Mont¹ K-10/800° C. | 181 | NC² | 22 | NC |
| 22 | Mont F-24/800° C. | 27 | NC | 0 | 3.35 |
| 23 | Mont K-10/200° C./vac | 0 | NC | 0 | 1.24 |
| 24 | Mont KSF/200° C./vac | 137 | 0.80 | 0 | 2.91 |
| 25 | Mont K-10/100° C./vac | 0 | 0.76 | 0 | 1.28 |
| 26 | Mont KSF/100° C./vac | 143 | 0.72 | 0 | 1.09 |
| 27 | Mont K-10/vac | 155 | NC | 19 | NC |
| 28 | Mont KSF/vac | 176 | NC | 13 | NC |
| 29 | Mont F-24/vac | 78 | NC | 3 | 0.75 |
| 30 | Mont G-62/vac | 71 | NC | 0 | 0.74 |
| Comparison | F-24/200° C./vac | 0 | 8.8 | 0 | 35.1 |
| Comparison | Mont /F-24/100° C./vac | 0 | 3.35 | 0 | 20.5 |

¹Mont = Montmorillonite
²NC = no change

EXAMPLES 31-36

In Examples 31-36 hexene-1 and octene-1 were treated with varying amounts of the montmorillonite K-10. The K-10 used for the hexene-1 treatment was treated in vacuum 1 m Hg for 2 hours at room temperature to reduce the water content. The results are shown in Table 5.

TABLE 5

Hexene-Octene-1 & Varying Amounts of Montmorillonite K-10
at Temp = 25° C.
(10 cm³ of Hexene-1/Octene-1)

| | | 1 hr | | 20 hrs | |
|---|---|---|---|---|---|
| Example | Olefin/g Mont K-10 | ppm diene | % 2-olefin | ppm diene | % 2-olefin |
| 31 | Hexene-1/1.0 g¹ | 155 | NC² | 19 | NC |
| 32 | Hexene-1/0.5 g¹ | 165 | NC | 37 | NC |
| 33 | Hexene-1/0.25 g¹ | 184 | NC | 109 | NC |
| 34 | Octene-1/1.0 | 251 | NC | 38 | NC |
| 35 | Octene-1/0.5 g | 282 | NC | 105 | NC |
| 36 | Octene-1/0.25 g | 339 | NC | 163 | NC |

¹Activated under vacuum at room temperature
²NC = no change

EXAMPLE 37

In Example 37 samples of octene-1 were treated, for six hours with undried montmorillonite K-10 at temperatures of 40° C., 50° C., and 60° C. The results in Table 6 show that heating the reaction increases the rate of conjugated diene removal.

TABLE 6

Octene-1 & Montmorillonite K-10 at
Temp = 40°, 50°, and 60° C.
(10 cm³ Octene-1 and 1 g Montmorillonite K-10)

| | ppm diene (initial - 480 ppm) | | |
|---|---|---|---|
| Time | Temp - 40° C. | Temp = 50° C. | Temp = 60° C. |
| 30 min | 176 | 122 | 55 |
| 1 hr | 158 | 74 | 40 |
| 2 hr | 111 | 52 | 37 |
| 4 hr | 71 | 42 | 32 |
| 6 hr | 55 | 41 | 32 |

EXAMPLE 38

Example 37 was repeated except that hexene-1 was used and the heating time at 40° C. was extended to 23 hours. The results are given in Table 7.

TABLE 7

Hexene-1 & Montmorillonite K-10 at
Temp = 40°, 50°, and 60° C.
(10 cm³ Hexene-1 and 1 g Montmorillonite)

| | ppm diene (initial - 200 ppm) | | |
|---|---|---|---|
| Time | Temp - 40° C. | Temp = 50° C. | Temp = 60° C. |
| 30 min | 189 | 179 | 147 |
| 1 hr | 183 | 159 | 71 |
| 2 hr | 168 | 125 | 12 |
| 4 hr | 149 | 38 | 0 |
| 6 hr | 124 | 18 | 0 |
| 23 hr | 35 | — | — |

EXAMPLES 39-42

Examples 39-42 demonstrate a continuous conjugated diene removal process in which the alpha-olefin, which had been dried using a molecular sieve column, was passed through the montmorillonite clay at different temperatures and flow rates. The process was carried out using four packed columns in series so that the process could be easily sampled at different lengths of exposure of the alpha-olefin to the catalyst clay. Each column contained an 18"×⅜ bed of montmorillonite and hexene-1 was fed from a supply to the top of the first column with a peristaltic pump. The process was run at four different flow rates with the temperature at 50° C. using montmorillonite F24 which had been vacuum dried at room temperature. The results are given in Table 8 for the effluent from the last column.

TABLE 8

| Example | Linear Flow mL/min | ppm Diene | % 2-Hexene | % Vinylidene |
|---|---|---|---|---|
| Control | — | 200 | 0.70 | 1.48 |
| 39 | 26 | 95 | 0.74 | 0.50 |
| 40 | 16 | 66 | 0.75 | 0.28 |
| 41 | 8 | 33 | 0.80 | 0.06 |
| 42 | 4 | 26 | 0.85 | 0.03 |

As noted in Table 8, the vinylidene content of the 1-hexene is also reduced by the treatment.

EXAMPLES 43–46

The continuous flow process was run to purify 1-hexene as in Examples 39–42, except that montmorillonite G-62 which had been vacuum dried at room temperature was used and the reaction temperature was 60° C. The results are given in Table 9.

TABLE 9

| Example[1] | Linear Flow mL/min | ppm Diene | % 2-Hexene |
|---|---|---|---|
| Control | — | 200 | 0.71 |
| 43 | 26 | 18 | 0.71 |
| 44 | 16 | 19 | 0.73 |
| 45 | 8 | 13 | 0.72 |
| 46 | 4 | 9 | 0.73 |

[1] % vinylidene = 0.03 for Examples 43–46.

EXAMPLE 47

Several long-term catalyst lifetime studies were performed using montmorillonite G-62 (Engelhard) and hexene-1 on the continuous flow reactor at a flow of 9 mL/min. An initial study at 60° C. showed very high levels of internals (8.5%) being formed after 22 hours of continuous operation. This was in marked contrast to the short-term studies which showed very little increase in internals at this temperature. The poor ratio of internal formation to diene removal continued even after cooling the system to 25° C. and running for several days. A possible cause of this result was believed to be due to water at the reactive site of the montmorillonite being either reacted or leached away. Therefore, several water doping runs were conducted to see if catalyst activity could be maintained at reasonable levels.

Three different water levels (120 ppm, 65 ppm, and 45 ppm) in the 1-hexene feed were tested at 50° C. using hexene-1 and G-62 with the molecular sieve drying column removed. In general, results after one hour showed that the drier the hexene-1, the greater the reactivity toward diene removal (52 ppm vs 30 ppm vs 4 ppm diene, respectively, after the last reactor column). The difference in reactivity dropped after 20 hours (60 ppm vs 31 ppm vs 27 ppm) and after 44 hours (111 ppm vs 84 ppm vs 94 ppm). Levels of internals remained relatively constant throughout all of these runs. When G-62 was tested with totally dried hexene-1 (run through a molecular sieve column) at 50° C., catalyst activity remained good for several days (1 hr—4 ppm; 20 hr—11 ppm; 44 hr—24 ppm; 68 hr—36 ppm; 92 hr—50 ppm after the last reactor column) and there was very little change in internals. Note that at flow=9.5 mL/min, the catalyst is purifying 160 bed volumes/day (LHSV—6.7 $hr^{-1}$).

It has been observed that the amount of water is critical to catalyst activity for montmorillonites—too much deactivates the catalyst for diene removal, but too little overactivites the catalyst regarding internals formation. The results of the above runs suggest that for successful long-term continuous operation using the montmorillonite G-62 there may be a critical temperature between 50° C. and 60° C. Accordingly, in any large-scale continuous flow reaction of hexene-1 and montmorillonite G-62 the temperature should be very carefully controlled to insure proper reactivity.

What is claimed is:

1. A process for improving a conjugated diene containing linear alpha-olefin product, said process comprising contacting said linear alpha-olefin product, which contains from about 100 to 1000 pm of conjugated dienes, with a montmorillonite clay, said clay consisting essentially of a montmorillonite clay which has been treated with an acid so as to replace alkali metal ions in the clay with hydrogen ions and which contains at least about 2 weight percent water, which clay is effective to reduce the conjugated diene content of said linear alpha-olefin product to less than about 100 ppm without substantial isomerization of the linear alpha-olefins to internal olefins.

2. The process of claim 1 wherein said linear alpha-olefin product comprises one or more linear alpha-olefins having from about 4 to 30 carbon atoms.

3. The process of claim 2 wherein said linear alpha-olefin product comprises hexene-1 and/or octene-1.

4. The process of claim 2 wherein said montmorillonite clay contains from about 2 to 20 weight percent water.

5. The process of claim 4 wherein said montmorillonite clay is pre-dried such that the clay contains from about 5 to 15 weight percent water.

6. The process of claim 2 wherein said linear alpha-olefin product is contacted with said montmorillonite clay at a temperature of from about 15° to 70° C.

7. The process of claim 1 wherein said contacting is by mixing said clay with said linear alpha-olefin product.

8. The process of claim 1 wherein said contacting is by passing said linear alpha-olefin product through a bed of said clay.

9. The process of claim 1 wherein said isomerization is less than about 0.5 wt. percent of the linear alpha-olefin product.

10. The process of claim 9 wherein said isomerization is less than about 0.05 wt. percent of linear alpha-olefin product.

* * * * *